US00PP16766P2

(12) United States Plant Patent
Herrington et al.

(10) Patent No.: US PP16,766 P2
(45) Date of Patent: Jul. 4, 2006

(54) STRAWBERRY PLANT NAMED 'QHI SUGARBABY'

(50) Latin Name: *Fragaria×ananassa*
Varietal Denomination: QHI Sugarbaby

(75) Inventors: Mark E. Herrington, Woombye (AU); Jennifer A. Moisander, Beenleigh (AU)

(73) Assignee: State of Queensland Through Its Department of Primary Industries, Queensland (AU)

( * ) Notice: Subject to any disclaimer, the term of this patent is extended or adjusted under 35 U.S.C. 154(b) by 123 days.

(21) Appl. No.: 10/850,375

(22) Filed: May 21, 2004

(30) Foreign Application Priority Data

May 27, 2003 (AU) ..... 2003/113

(51) Int. Cl.
*A01H 5/00* (2006.01)

(52) U.S. Cl. ..... Plt./208
(58) Field of Classification Search ..... Plt./208
See application file for complete search history.

(56) References Cited

U.S. PATENT DOCUMENTS

PP5,266 P * 7/1984 Bringhurst et al. ..... Plt./209
PP8,708 P * 5/1994 Voth et al. ..... Plt./209
PP8,729 P * 5/1994 Howard ..... Plt./208
PP14,739 P2 * 4/2004 Chandler ..... Plt./208

OTHER PUBLICATIONS

UPOV ROM GTITM Computer Database, GTI Jouve Retrieval Software 2005/03 Citation for 'QHI Sugarbaby'.*

* cited by examiner

*Primary Examiner*—Kent Bell
*Assistant Examiner*—W. C. Haas
(74) *Attorney, Agent, or Firm*—Buchanan Ingersoll PC

(57) ABSTRACT

A new and distinct short-day strawberry cultivar is provided. Attractive medium-sized generally conical to cordiform sweet and flavorful fruit with firm flesh is formed in good yields. The fruit is glossy bright red on the outside and medium red on the inside. Resistance to *Fusarium* Wilt is displayed. The fruiting pattern and yield are similar to the 'Camarosa' cultivar (U.S. Plant Pat. No. 8,708) and commonly fruits later than the 'Sweet Charlie' (U.S. Plant Pat. No. 8,729) and 'Strawberry Festival' (U.S. Plant Pat. No. 14,739) cultivars.

3 Drawing Sheets

Figure 1:
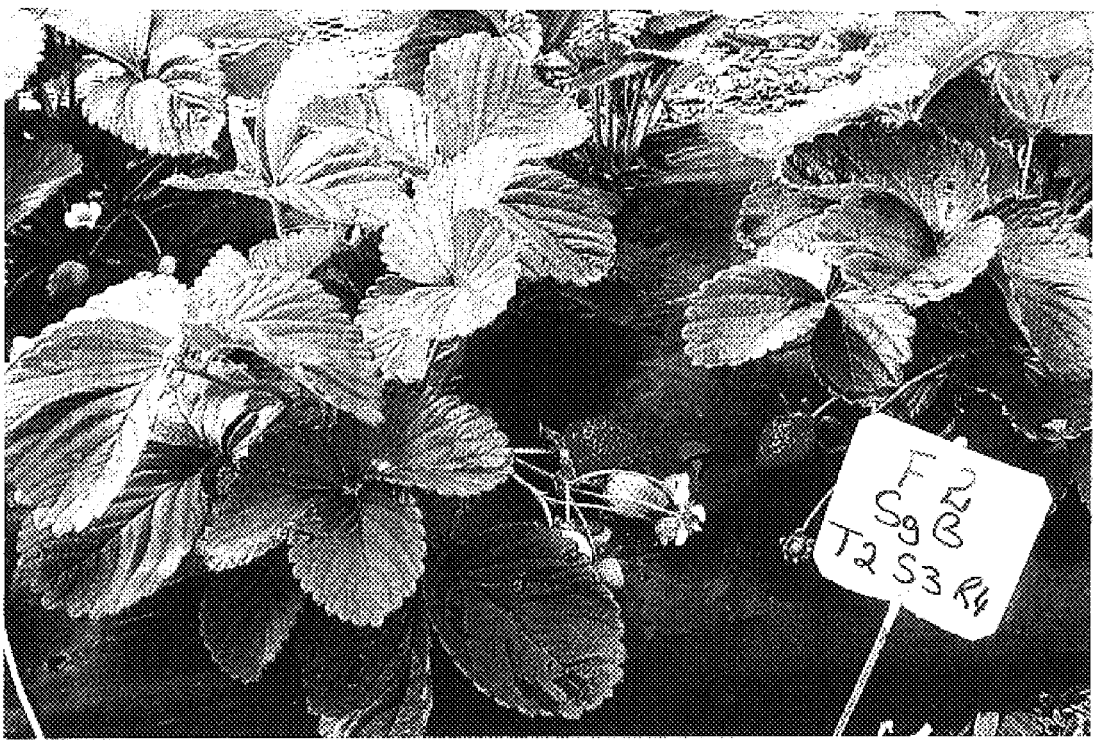

Botanical/commercial classification: *Fragaria×ananassa* Duchesne/Strawberry Plant.
Varietal denomination: cv. 'QHI Sugarbaby'.

SUMMARY OF THE INVENTION

The new and distinct short day strawberry cultivar of the present invention was the product of a controlled breeding program carried out at Nambour, Queensland, Australia (27° S., 153° E.). The seed parent (i.e., the female parent) was the 'Coogee' cultivar (non-patented in the United States), and the pollen parent (i.e., the male parent) was the 'Redlands Joy' cultivar (non-patented in the United States). In Australia the 'Redlands Joy' cultivar is the subject of the Plant Breeder's Rights Application 1992/088.

The seeds resulting from this cross were germinated and the resulting seedlings were transplanted to raised beds where they fruited and were subjected to detailed evaluation. During the 2000 season from among approximately 5,700 of the resulting seedlings, a seedling designated 2000-430 was chosen primarily on the basis of its superior fruit appearance and flavor. This seedling was further advanced through plot selection trials during 2001–2002. During such trials the selection criteria included yield, yield distribution, fruit size, fruit shape, external and internal fruit color, fruit resistance to bruising and abrasion, fruit shelf life, fruit flavor, overall fruit attractiveness, tolerance to disease and rain damage, plant bush type, ease of harvest, truss type, and propensity for runner production. As a result of this evaluation, a single plant of the present invention has been selected. Such plant further has been virus indexed.

It was found that the new strawberry plant of the present invention exhibits the following combination of characteristics:

(a) is a short-day cultivar,
(b) forms attractive medium-sized generally conical to cordiform sweet and flavorful fruit with firm flesh in good yields that is glossy bright red on the outside and medium red on the inside,
(c) displays a fruiting pattern and yield similar to the 'Camarosa' cultivar (U.S. Plant Pat. No. 8,708) and commonly fruits later than the 'Sweet Charlie' (U.S. Plant Pat. No. 8,729) and 'Strawberry Festival' (U.S. Plant Pat. No. 14,739) cultivars, and
(d) displays resistance to *Fusarium* wilt.

The preferred planting date is April $2^{nd}$ to April $9^{th}$ at southeastern Queensland, Australia.

The new cultivar of the present invention can be readily distinguished from previously grown strawberry cultivars as indicated by the combination of characteristics that is specified hereafter.

The new cultivar possesses characteristics that commonly are sought by commercial strawberry growers. A highly favorable fruit Brix/Acid balance is displayed which has been well received during taste evaluations to date. Accordingly, the new cultivar is a promising candidate for commercial success since it produces flavorful and attractive fruit that well retains its desirable attributes even following long-distance shipment.

The new cultivar has been asexually reproduced by use of runners and by tissue culture at Applethorpe, Queensland, Australia. The combination of characteristics exhibited by this new plant has been found to be stable and is reliably transmitted to succeeding generations following such asexual reproduction. Accordingly, the new cultivar reproduces true to type by such asexual reproduction.

The new plant of the present invention has been named 'QHI Sugarbaby'.

BRIEF DESCRIPTION OF THE PHOTOGRAPHS

The accompanying photographs show, as nearly true as it is reasonably possible to make the same in color illustrations of this character, typical specimens of the new cultivar. The illustrated plants have been reproduced by the use of runners and were being grown outdoors in full sun at Cleveland (FIG. 1) and Nambour (FIGS. 2 and 3), Queensland, Australia.

FIG. 1 illustrates typical specimens of fruiting plants of the new cultivar. Such plants were photographed approximately 10 weeks following transplanting.

Figure 2:
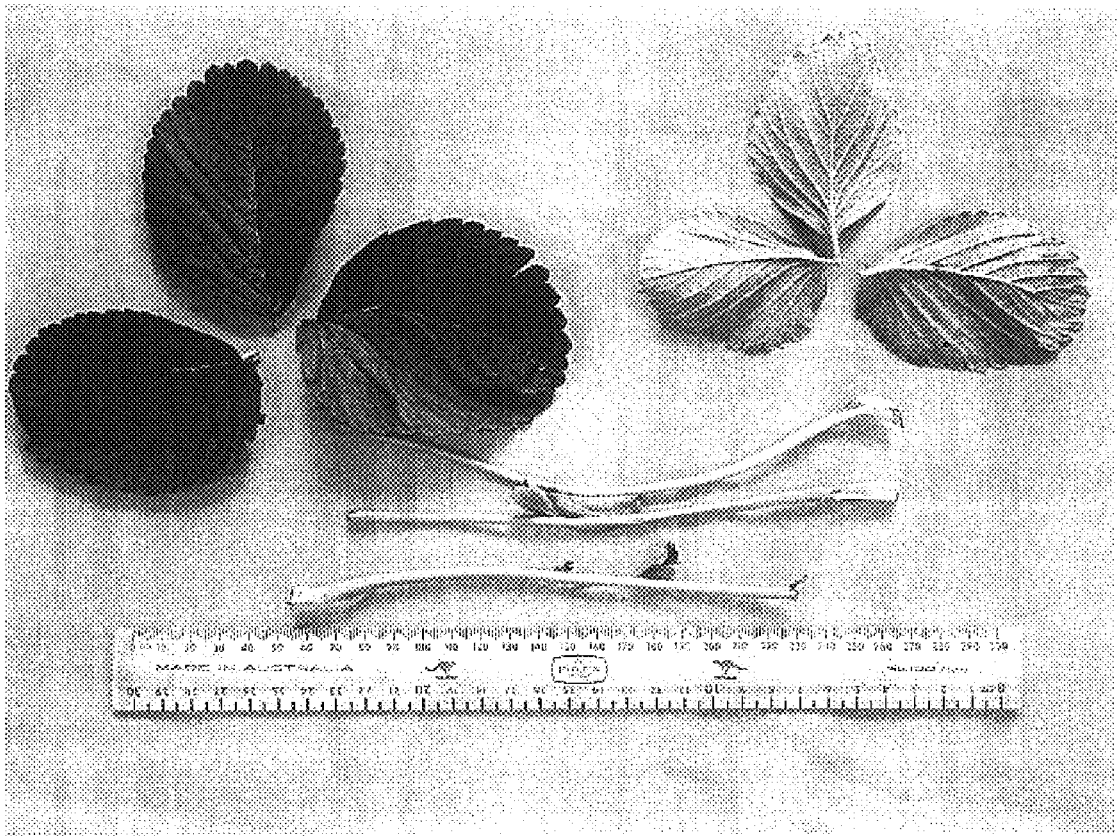

FIG. 2 illustrates typical specimens of leaves of the new cultivar with upper surfaces being shown at the left and under surfaces being shown at the right, as well as typical stems. These plant parts were obtained from plants of the new cultivar approximately 26 weeks following transplanting. Measurements in centimeters and millimeters are included at the bottom of the photograph.

Figure 3:
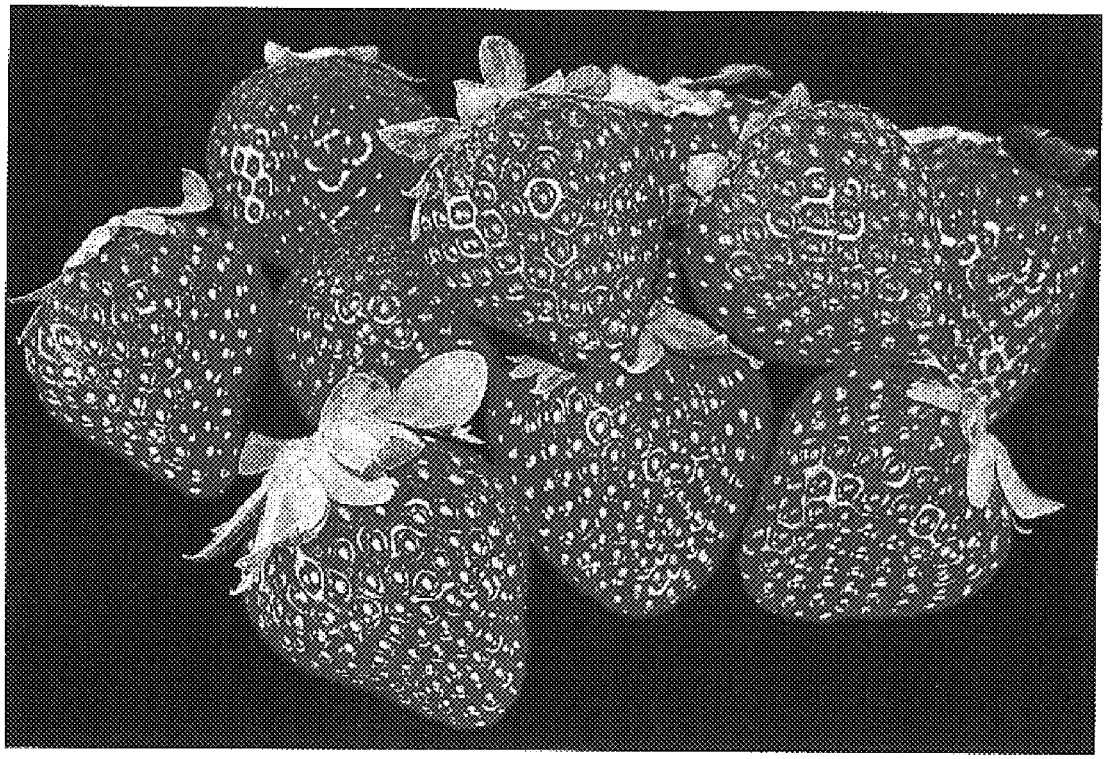

FIG. 3 illustrates typical specimens of the attractive medium-sized generally conical to cordiform bright red fruit of the new cultivar.

DETAILED DESCRIPTION

The described plants had been asexually reproduced by the use of runners, and had been planted outdoors during early April at Nambour, Queensland, Australia. The chart used in the identification of color is The R.H.S. Colour Chart of The Royal Horticultural Society, London, England (1995). Reference to common color terms is to be accorded ordinary dictionary significance.

Botanical class: *Fragaria×ananassa* Duchesne, cv. 'QHI Sugarbaby'.

Plant:

*Type.*—Short-day.

*Configuration.*—Globose and open plant density.

*Vigor.*—Strong.

*Height.*—Approximately 27 cm on average six months after planting.

*Width.*—Approximately 38 cm on average six months after planting.

Foliage:

*Size.*—Initially the terminal leaflets are substantially the same in length and breadth and commonly display an average length of approximately 65 mm and an average width of approximately 63 mm. In the summer the terminal leaflets commonly display an average length of approximately 90 mm and an average width of approximately 84 mm. In the summer the secondary leaflets commonly display an average length of approximately 90 mm and an average width of approximately 87 mm.

*Margin.*—Commonly crenate.

*Serration.*—Approximately 26 serrations on average on terminal leaflets and approximately 28 serrations on average on secondary leaflets (as illustrated in FIG. 2).

*Shape.*—Substantially orbicular.

*Base.*—Obtuse.

*Cross-section.*—Slightly concave.

*Blistering.*—Absent or very weak.

*Glossiness.*—Weak.

*Color.*—Upper Surface: Medium green, Yellow-Green Group 146A. Under Surface: Light grey green, Green Group 138B.

*Petiole texture.*—Medium pubescence with hairs directed slightly outwards.

*Petiole color.*—Yellow-Green Group 144B.

*Petiole length.*—Approximately 26.5 cm on average.

*Petiole diameter.*—Approximately 3.4 cm on average.

*Stipules.*—Length: Approximately 3.2 cm on average. Width: Approximately 8 mm on average. Shape: Trapezoid. Apex: Acute Base: Generally flat. Margin: Smooth. Color: Red-Purple Group 57C on the outer surface, and Red-Purple Group 57C on the inner surface.

*Stolons.*—Medium presence, primarly stolons commonly number approximately 25 per plant on average, and the total number of stolons per plant commonly is approximately 80 on average.

Inflorescence:

*Flowering time.*—Late, a first flowering date of May 7th and a last flowering date of October 7th have been observed.

*Chilling requirement.*—No chilling is required to flower.

*Position.*—Approximately at canopy height.

*Number.*—Commonly approximately 8 flowers on average per inflorescence.

*Size.*—Large and approximately 35 mm in diameter on average.

*Depth.*—Flowers commonly display a depth of approximately 10 mm on average.

*Petal number.*—Six.

*Petal shape.*—Flattened ellipse.

*Petal arrangement.*—Overlapping.

*Petal length.*—Approximately 14.3 mm on average.

*Petal width.*—Approximately 15.6 mm on average.

*Petal base.*—Rounded.

*Petal apex.*—Rounded.

*Petal margin.*—Smooth.

*Petal color.*—White Group 155D.

*Stamen number.*—Approximately 26 on average.

*Filament color.*—Green-White Group 157B.

*Anther color.*—Yellow-Green Group 153D.

*Pollen quantity.*—Moderately abundant.

*Pollen color.*—Yellow Group 13A.

*Pistil number.*—Approximately 300 on average.

*Style color.*—Yellow-Green Group 154A.

*Stigma color.*—Yellow-Green Group 150C.

*Calyx type.*—Commonly smaller relative to the corolla, possesses spreading segments, approximately the same size as the fruit diameter, substantially level with the first, and strongly adhering.

*Calyx diameter.*—Commonly approximately 3.3 cm on average.

*Calyx color.*—Green Group 138B on the upper surface and Green Group 139B on the under surface.

*Sepal number.*—Twelve.

*Sepal shape.*—Much larger than broad and commonly display a length to breadth ratio of approximately 1:2.9.

*Sepal apex.*—Acute.

*Sepal base.*—Flat.

*Sepal margin.*—Mostly entire and smooth, and commonly bears one or two indentations.

Fruit:

*Bearing.*—Partially remontant.

*Time.*—First fruiting has occurred on June 1st and last fruiting on November 1st.

*Shape.*—Generally conical to cordiform and approximately the same in length and width.

*Length.*—Approximately 36.3 mm on average.

*Width.*—Approximately 34.8 mm on average.

*Weight.*—Medium and commonly approximately 18 g on average, smaller than the 'Camarosa' cultivar, similar to the 'Strawberry Festival' and 'Redlands Joy' cultivars, and larger than the 'Sweet Charlie' cultivar (see Tables 1 and 2 hereafter).

*Achenes.*—Below fruit surface.

*Glossiness.*—Strong.

*External color.*—Bright red, Red Group 45A.

*Internal color.*—Medium red, Red Group 45B, and substantially evenly distributed throughout.

*Fruit center.*—Solid with little or no hollowness, and very firm.

*Brix.*—Moderate and about the same as the 'Sweet Charlie' cultivar.

*Acidity.*—Low and similar to that of the 'Sweet Charlie' cultivar, lower than the 'Strawberry Festival', and much lower than the 'Camarosa' cultivar (see Table 3 hereafter).

*Fruiting.*—In replicated trials during 2003 the fruiting was similar to that of the 'Camarosa' cultivar and later than the 'Sweet Charlie' and 'Strawberry Festival' cultivars (see Table 2).

*Yield.*—Somewhat lower total yields than the 'Redlands Joy' cultivar during 2002 (see Table 1). In replicated trials during 2003 the yield was generally comparable to the 'Redlands Joy', 'Camarosa' and 'Sweet Charlie' cultivars and less than that of the 'Strawberry Festival' cultivar (see Table 2).

Disease resistance: The new cultivar has been shown to be highly resistant to *Fusarium* wilt (caused by *Fusarium oxysporum* Schlecht. ex Fr. f sp. *fragariae*, Winks and Williams) during observations to date. Such resistance is similar to that of the 'Strawberry Festival' and 'Sweet Charlie' cultivars, and much more resistant than the 'Selva' (U.S. Plant Pat. No. 5,266) and 'Camarosa' cultivars (See Table 4 hereafter). The relative susceptibility to Anthracnose Fruit Rot (caused by *Colletotrichum actuatatum* Simmonds), *Colletotrichum* Crown Rot (caused by *Colletotrichum gloeosporodies* Penz.), Angular Leaf Spot (caused by *Xanthomonas fragariae* Kennedy & King), Botrytis Fruit Rot (caused by *Botrytis cinerea* Pers. ex Fr.), Powdery Mildew (caused by *Sphaerotheca macularis* [Wallr. ex Fr.] Jacz. f. sp. *fragariae*) and to the Two-spotted Spider Mite (*Tetranychus urtricae* Koch) has not been determined since serious infestations of these have not yet been observed where appropriate control measures, such as clean planting material and predatory mite releases, have been utilized.

The following Table 1 provides yield information for plants of the 'QHI Sugarbaby' cultivar and the 'Redlands Joy' cultivar for comparative purposes during 2002.

TABLE 1

| Cultivar | Mean Yield to End of June (g/plant) | Mean Yield to End of July (g/plant) | Mean Yield to End of August (g/plant) | Mean Fruit Size (g) |
|---|---|---|---|---|
| 'QHI Sugarbaby' | 10 | 90 | 226 | 13.2 |
| 'Redlands Joy' | 55 | 186 | 358 | 14 |

The following Table 2 provides typical yield information for plants of the 'QHI Sugarbaby' cultivar and the 'Redlands Joy', 'Strawberry Festival', 'Camarosa', and 'Sweet Charlie' cultivars for comparative purposes during 2003.

TABLE 2

| Cultivar | Mean Yield to End of May (g/plant) | Mean Yield to End of June (g/plant) | Mean Yield to End of July (g/plant) | Mean Yield to End of August (g/plant) | Mean Fruit Size (g) |
|---|---|---|---|---|---|
| 'QHI Sugarbaby' | 0 | 25 | 171 | 368 | 18.1 |
| 'Redlands Joy' | 0 | 33 | 213 | 384 | 19.6 |
| 'Strawberry Festival' | 0 | 102 | 332 | 481 | 19.4 |
| 'Camarosa' | 0 | 25 | 158 | 324 | 23.7 |
| 'Sweet Charlie' | 0 | 101 | 291 | 396 | 13.4 |

The following Table 3 provides Brix and Acid values for the mature randomly harvested fruit of the 'QHI Sugarbaby' cultivar and the 'Redlands Joy', 'Camarosa' and 'Sweet Charlie' cultivars for comparative purposes. The fruit was harvested on Jul. 1 and 2, 2003, was frozen, and was assessed on Feb. 9, 2004. The Brix was a standard refractometer measure, and the Acid value was measured as titratable acidity in percent citric acid equivalents.

TABLE 3

| Cultivar | Brix | Acid |
|---|---|---|
| 'QHI Sugarbaby' | 8.9 | 0.51 |
| 'Redlands Joy' | 8.5 | 0.62 |
| 'Camarosa' | 7.9 | 0.74 |
| 'Sweet Charlie' | 8.7 | 0.58 |

The fruit of the new cultivar is sweet and flavorful.

The following Table 4 provides disease reaction information with respect to *Fusarium* Wilt for the 'QHI Sugarbaby' cultivar and for the 'Strawberry Festival', 'Sweet Charlie', 'Camarosa', and 'Selva' cultivars for comparative purposes. Plants were planted in contaminated soil during April 2003 and an assessment of each plant was made on Oct. 14, 2003. A Disease Reaction Rating of 1 to 10 was utilized where 0 indicates completely healthy and vigorous, 1 indicates trace impairment, 3 indicates slight unhealthiness, 5 indicates moderate unhealthiness, 7 indicates substantial unhealthiness, and 10 indicates plant death.

TABLE 4

| Cultivar | Disease Reaction Rating |
|---|---|
| 'QHI Sugarbaby' | 0.3 |
| 'Strawberry Festival' | 0.6 |
| 'Sweet Charlie' | 1.0 |
| 'Camarosa' | 2.3 |
| 'Selva' | 3.2 |

Accordingly, the new cultivar of the present invention displays superior resistance to *Fusarium* Wilt.

We claim:

1. A new and distinct strawberry plant that exhibits the following combination of characteristics:

(a) is a short-day cultivar, (b) forms attractive medium-sized generally conical to cordiform sweet and flavorful fruit with firm flesh in good yields that is glossy bright red on the outside and medium red on the inside, (c) displays a fruiting pattern and yield similar to the 'Camarosa' cultivar (U.S. Plant Pat. No. 8,708) and commonly fruits later than that of the 'Sweet Charlie' (U.S. Plant Pat. No. 8,729) and 'Strawberry Festival' (U.S. Plant Pat. No. 14,739) cultivars, and (d) displays resistance to *Fusarium* wilt;

substantially as illustrated and described.

* * * * *